(12) United States Patent
Taicher et al.

(10) Patent No.: US 7,355,402 B1
(45) Date of Patent: Apr. 8, 2008

(54) METHOD AND APPARATUS FOR HAZARDOUS LIQUID DETECTION

(75) Inventors: Gersh Z. Taicher, Houston, TX (US); Zinovy Krugliak, Houston, TX (US); Israel Kovner, Houston, TX (US); Andrei Baikalov, Houston, TX (US)

(73) Assignee: Echo Medical Systems, LLC, Houston, TX (US)

( * ) Notice: Subject to any disclaimer, the term of this patent is extended or adjusted under 35 U.S.C. 154(b) by 0 days.

(21) Appl. No.: 11/602,895

(22) Filed: Nov. 20, 2006

(51) Int. Cl.
*G01V 3/00* (2006.01)
(52) U.S. Cl. ...................................... 324/300; 324/307
(58) Field of Classification Search ........ 324/300–322; 600/407–455
See application file for complete search history.

(56) References Cited

U.S. PATENT DOCUMENTS

| | | | |
|---|---|---|---|
| 6,194,900 B1* | 2/2001 | Freeman et al. | 324/321 |
| 6,268,724 B1* | 7/2001 | Crowley | 324/243 |
| 6,333,629 B1* | 12/2001 | Pykett et al. | 324/307 |
| 6,344,818 B1* | 2/2002 | Markov | 342/22 |
| 6,891,369 B2* | 5/2005 | Hurlimann et al. | 324/303 |
| 2005/0202570 A1* | 9/2005 | Pusiol | 436/173 |
| 2006/0017605 A1* | 1/2006 | Lovberg et al. | 342/22 |
| 2007/0241753 A1* | 10/2007 | Sodickson et al. | 324/307 |

* cited by examiner

*Primary Examiner*—Brij Shrivastav
(74) *Attorney, Agent, or Firm*—Richard A Fagin (57) ABSTRACT

A method for hazardous liquid detection within a container includes inducing a static magnetic field in the container, inducing a radio frequency magnetic field in the container at a frequency selected to excite nuclear magnetic resonance phenomena in liquids; detecting nuclear magnetic resonance signals from the container and analyzing the signals for presence of liquids above a threshold mass.

13 Claims, 12 Drawing Sheets

METHOD AND APPARATUS FOR HAZARDOUS LIQUID DETECTION

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The invention is related to the field of Nuclear Magnetic Resonance (NMR) and Magnetic Resonance Imaging (MRI) apparatus and methods. More particularly, the invention relates to apparatus and methods for detecting explosives and flammable liquids.

2. Background Art

The description of the invention and its background are explained herein in the context of screening devices for detecting liquids being carried by passengers into the passenger cabin of an aircraft.

In a response to terror plots, authorities across the world have placed extreme limits on liquid items being taken through passenger security checkpoints onto commercial aircraft. The authorities have banned things such as hair gels, deodorants, ointments, chapped lip remedies, aerosols, etc. from being carried by passengers into the passenger cabin on all commercial airline flights. In light of this, it is obvious that a liquid detection system is very important and should be employed in conjunction with other effective screening devices at passenger checkpoints, throughout the world's airports.

X-ray screening systems and metal detectors are known in the art for detecting contraband that could be physically used as weapons. An example of an x-ray system is described in U.S. Pat. No. 7,092,485 issued to Kravis. Such a system includes combined angular and energy dispersive x-ray scanning to detect the presence of a contraband substance within an interrogation volume of a baggage item. The interrogation volume is illuminated with penetrating, polychromatic x-rays in a primary fan beam from a source such as a tungsten-anode x-ray tube. An energy-dependent absorption correction is determined from measurement of the attenuation of the fan beam at a plurality of different energies. Radiation coherently scattered by substances in the interrogation volume is detected by an energy-resolved x-ray detector operated at a plurality of scattering angles to form a plurality of scattering spectra. Each scattering spectrum is corrected for energy-dependent absorption and the corrected spectra are combined to produce a scattering pattern. The experimental scattering pattern is compared with reference patterns that uniquely characterize known contraband substances. The system and method can locate and identify a wide variety of contraband substances in an accurate, reliable manner. The system provides for automated screening, with the result that vagaries of human performance are virtually eliminated. False alarms and the need for hand inspection are reduced and detection efficacy is increased.

However, neither X-ray devices nor any other technology known in the art can effectively detect liquids and liquid-based explosives compound. Special difficulties are associated with the detection of liquids soaked in cloth which may not be resolved by x-ray scanning techniques.

NMR methods related to plastic explosive detection are described in U.S. Pat. No. 4,514,691 issued to De Los Santos, et al. A method and apparatus disclosed in the '691 patent are directed to baggage inspection. A conveyor system is utilized to transport a bag past a first magnet to achieve an initial nuclear magnetic resonance (NMR) polarization of a selected element. The selected element in the preferred embodiment is hydrogen, it being noted that hydrogen in explosives has a long longitudinal relaxation time ($T_1$) and a short transverse relaxation time ($T_2$). The first magnet provides an initial polarization. The bag continues on the conveyor belt past a second magnet. The second magnet provides the measurement field intensity and a coil contains an interacting RF forming the interrogation pulses. Nuclear magnetic spin echoes are generated and received as a result of the interrogating pulses. First and subsequent second echoes are received and stored. The two signals are subtracted from one another to a null. The NMR response of elemental hydrogen in compounds typified by explosives is accented by subtraction of the two stored signals to form a response indicative of explosive materials. The apparatus includes means for adjusting the magnetic field to accommodate distortions for metal in the baggage.

A method related to plastic explosive detection is described in U.S. Pat. No. 6,194,898 issued to Magnuson et al. A system disclosed in the '898 patent detects a target substance within a class of explosives and narcotics containing quadrupolar nuclei through the use of nuclear quadrupole resonance (NQR). The system applies an RF signal to a coil to excite the substance under test. If the target material is present, an NQR signal will be picked up by the same coil. That signal is compared with known NQR signals in frequency and amplitude. A signal is displayed in an appropriate way if a threshold value of the NQR signal is exceeded. The empty coil is statically tuned by means of adjusting the location or capacitance values, or both, of static tuning capacitors in the coil. The coil is tuned after the specimen is inserted into the coil by means of an auto-tune feature. Effective RFI shielding is provided to prevent external contaminating signals from being detected by the coil and to prevent RF signals from escaping from the scanner. The invention also includes the method for performing tests with the system.

Prior art detecting devices are directed to determining the presence of metals and/or plastic explosives in carry-on baggage. While effective at deterring such materials from being carried onto aircraft, other threats, namely hazardous liquids, have become known. Plastic explosives, for example, are necessary to be carried in large amounts to represent an actual threat to an aircraft. Some sort of metallic detonator must be used for initiation of plastic explosive and would therefore be expected to be found in carry on baggage items subjected to ordinary screening. Liquids, however, may be poured together from small containers into a large one and be ignited or detonated one on board an aircraft. As explained above detection of liquids using techniques known in the art has proven difficult because of the low density contrast with harmless carry on items and the fact that hazardous liquids may be soaked into articles of clothing or separated into smaller containers and distributed throughout a piece of carry on baggage making them difficult to detect.

What is needed is a system for rapidly detecting liquids and characterizing them as safe or hazardous so as to reduce the number of visual inspections of passengers and carry on articles when loading aircraft.

SUMMARY OF THE INVENTION

One aspect of the invention is a method for hazardous liquid detection within a container. A method according to this aspect of the invention includes inducing a static magnetic field in the container, inducing a radio frequency magnetic field in the container at a frequency selected to excite nuclear magnetic resonance phenomena in liquids; detecting nuclear magnetic resonance signals from the container and analyzing the signals for presence of liquids above a threshold mass.

A method for screening personal items for presence of safety hazards according to another aspect of the invention includes x-ray scanning the personal articles for presence of high-density objects. The items are then nuclear magnetic resonance scanned for presence of liquids above a threshold mass. The items are nuclear magnetic resonance scanned to estimate composition of liquids detected above the threshold mass. The items are nuclear magnetic resonance scanned to determined spatial distribution of liquids detected above the threshold mass. Any of the personal items for which the x-ray scanning, nuclear magnetic resonance scanning for liquids above the threshold mass, nuclear magnetic resonance scanning for composition and nuclear magnetic resonance scanning for spatial distribution indicates a combined threat level above a selected threshold are selected for opening and inspection.

A system for screening human subjects for presence of liquids according to another aspect of the invention includes a room sufficiently large to enable free ingress and egress of a largest expected human subject. At least one electromagnet coil is wound to induce a substantially homogeneous magnetic field along a selected direction within a selected volume within the room. At least one radio frequency antenna is configured to induce a substantially homogeneous magnetic field in the selected volume along a direction substantially perpendicular to the selected direction of the static magnetic field. The system includes means for energizing the at least one electromagnet coil and the radio frequency antenna to induce respective magnetic fields. The system includes a first receiver antenna configured to detect nuclear magnetic signals originating proximate a first face of a human subject disposed proximate thereto and a second receiver antenna arranged to detect nuclear magnetic resonance signals originating proximate an opposed face of the human subject. The system includes means for analyzing the detected signals to determine presence of at least a threshold mass of liquid proximate at least one of the first and opposed faces of the human subject.

A method for security screening a human subject according to another aspect of the invention includes inducing nuclear magnetic resonance phenomena in selected nuclei associated with liquids in the human subject and detecting nuclear magnetic resonance signals originating proximate the surface of the human subject. The detected signals are analyzed to determine at least one of presence of a threshold mass of liquid and a spatial distribution of liquid about the person of the human subject.

Other aspects and advantages of the invention will be apparent from the description and claims that follow.

DETAILED DESCRIPTION

A system and method for hazardous liquid detection in various aspects of the invention can include two distinct parts. One part is a screening device for personal items. The other part is a screening device for on-body (passenger) objects.

This invention is not intended to identify all materials disposed within a closed container. Rather, the purpose of the invention is to assess a risk level of the presence of hazardous liquids within in closed containers as quickly as possible, so as to separate those containers deemed to have at least a threshold threat level for opening and inspection. More specifically, the intent of the invention is to reduce false-negative response in closed container screening to substantially zero and thus to reduce the number of containers that must be hand screened by at least an order of a magnitude. Such improvement of false-negative screening may have as a benefit a substantial improvement in the efficiency with which passengers and their personal items may be security screened for aircraft loading.

Figure 1:
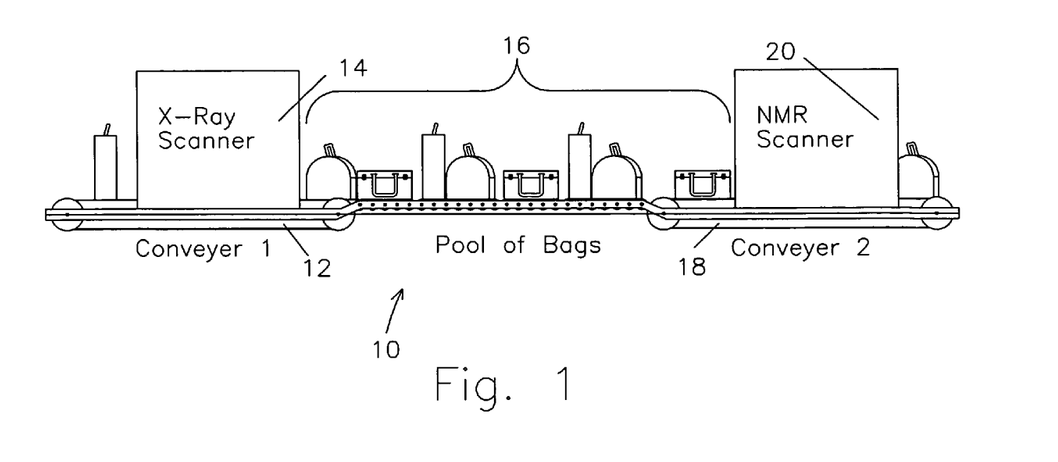
FIG. 1 shows an example embodiment of a modular hazardous substance detection system apparatus according to the invention.

An example embodiment of a screening system according to one aspect of the invention is shown schematically in FIG. 1. The system 10 includes a first conveyor 12 which conducts personal items through a conventional x-ray screening device 14. The x-ray screening device 14 may be of a type requiring visual interpretation of the contents of the personal items by the device operator, as is well known in the art. The outlet of the first conveyor may conduct x-ray screened items to a storage buffer or pool 16. The pool 16 provides temporary storage for personal items after x-ray screening before such personal items are conducted by a second conveyor 18 into a nuclear magnetic resonance (NMR) screening device, shown generally at 20. As will be further explained in more detail below, as each personal item is introduced into the NMR screening device, an initial, high speed evaluation for the presence of liquids may be performed. Personal items which do not show presence of total mass of liquids above a predetermined threshold may be released to the passengers responsible for such personal items. In the event a total liquid mass is determined to be above a selected threshold in any one or more personal items, such item may then be subjected to a more rigorous analysis in the NMR screening device 20. Such more rigorous analysis requires additional scanning time, during which time additional personal articles may enter the pool 16 after x-ray screening.

Figure 2:
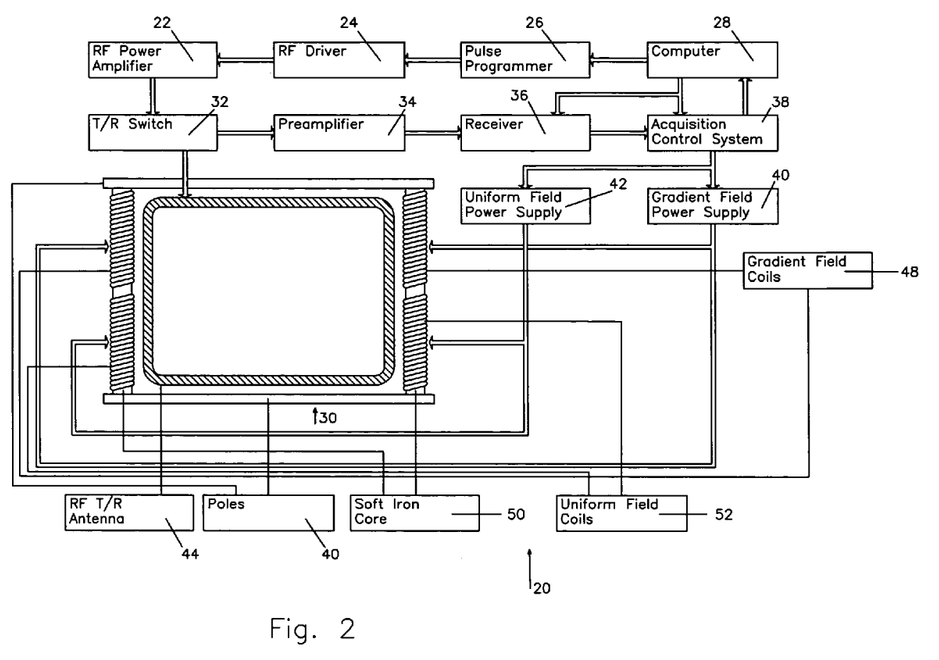
FIG. 2 shows one embodiment of an NMR screening device that may be used alone or with the system shown in FIG. 1.

An example embodiment of the NMR screening device 20 is shown schematically in FIG. 2. The NMR screening device 20 may include an inspection chamber 30 through which personal articles are passed by the second conveyor (18 in FIG. 1). The inspection chamber 30 is shown in end view in FIG. 2, and includes a magnet for inducing a substantially homogeneous static magnetic field within the chamber 30. In the present embodiment the magnet can be an electromagnet consisting of wire coils 52 wound around soft iron coil supports 50. The coils 52 and supports 50 are generally oriented along a common direction, which may be substantially perpendicular to a direction of motion of the personal items through the chamber 30 during inspection. At the longitudinal ends of the coils 52 and supports 50, the magnet includes ferromagnetic poles 45 which serve to produce a substantially homogeneous static magnetic field within the chamber 30 when electrical current is passed through the coils 52. Generally the polarization of the static magnetic field will be between the poles 45. A static magnetic field power supply 42 may be used to energize the coils 52. Amplitude of the static magnetic field may be varied in some embodiments as will be further explained, by changing the current applied to the coils 52. In the present embodiment, the coils supports 50 may include gradient field coils 48. The gradient field coils 48 may be energized by a gradient field power supply 40. In some embodiments, as will be further explained, a gradient field may be superimposed on the homogeneous magnetic field in order to measure NMR properties related to the diffusion characteristics of any liquids detected in the chamber 30 during screening. The chamber 30 includes a radio frequency (RF) transmit/receive antenna 44 that may be electrically coupled to a transmit/receive switch 32. Generally, the antenna 44 is in the form of a wire coil wound so that a magnetic dipole moment of the antenna is transverse to polarization direction of the static homogeneous magnetic field induced by the magnet (through coils 52 and poles 46). As shown in FIG. 2, such dipole moment is generally coaxial with the longitudinal axis of the chamber 30.

The antenna 44 is arranged such that when RF power pulses of a selected frequency are passed through the antenna 44, NMR phenomena are excited in certain nuclei of substances disposed in the chamber (which substances are intended to be personal articles carried by the second conveyor [18 in FIG. 1]). Such RF power pulses are generated by a pulse programmer 26, which may be under control of a system computer 28. Output of the pulse programmer 26 may be conducted to the input of an RF driver 24. The output of the RF driver 24 may be coupled to the input of an RF power amplifier 22, and ultimately to the T/R switch 32. The T/R switch 32 may be under control of the computer 28, and configured to connect the antenna 44 to the RF power amplifier 22 during times at which power pulses are to be conducted through the antenna 44. During other time intervals, the T/R switch 32 may be operated to connect the antenna 44 to the input of a preamplifier 34. The preamplifier 34 may be connected at its output to an RF receiver 36 which detects certain attributes of voltages induced in the antenna 44 by NMR phenomena excited in the articles disposed in the chamber 30. Operation of the receiver 36, and the two magnet power supplies 42, 40 may be controlled by an acquisition control unit 38, which itself may be controlled by the computer 28. The functional elements of the system shown in FIG. 2 are well known in the art of NMR measurement systems. Distinguishing details of the system as applied to detection of liquids in closed containers will now be further explained.

Figure 3:
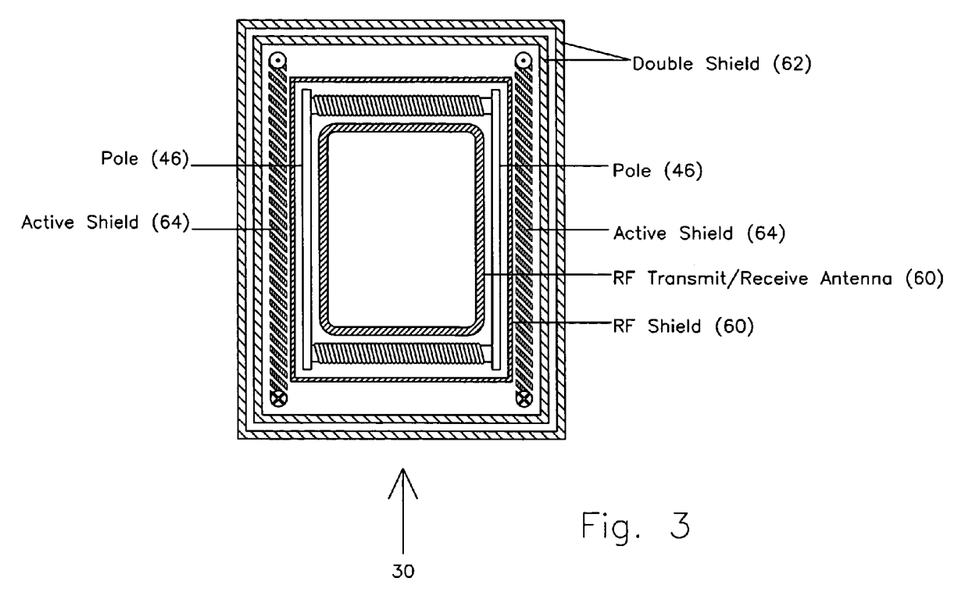
FIG. 3 shows a side view of the inspection chamber of the device shown in FIG. 2.

FIG. 3 shows a detailed end view of the chamber 30. In inspection of personal items in a pubic area, it is desirable to reduce as far as is practicable the exposure of persons to electromagnetic radiation and static magnetic fields. The present embodiment includes features intended to accomplish such objectives. As is known in the art, the frequency of the RF magnetic fields used to induce NMR phenomena depends on the particular nucleus investigated, which in the present implementation is hydrogen, and the amplitude of the static magnetic field used to polarize the investigated nuclei. In the present embodiment, the system forms a NMR relaxometer, which preferably operates using RF in the in range of about 0.1 to 5 MHz. The corresponding amplitude of the static, homogeneous magnetic field needed with such low frequency is such that by using certain features shown in FIG. 3, it is possible to have a 5 Gauss static magnetic field amplitude substantially at the exterior surface of the components forming the chamber 30.

Low magnetic field is also preferable because small ferromagnetic objects, such as made from steel, may be disposed within an inspected item. Presence of such objects reduces the static magnetic field homogeneity, and in the worst case changes the field amplitude. Moreover, the presence of liquids may be obscured by relatively small amounts of such ferromagnetic material, such as heel inserts found in shoes. Large steel objects will be detected by the x-ray screening device (14 in FIG. 1), resulting in selection of the affected item for visual inspection and are thus generally not relevant to operation of the NMR screening device. In the present embodiment, the existence of small ferromagnetic objects and/or electrically conductive objects in inspected items may be accounted for by having relatively large magnet gap, having the static magnetic field be low amplitude, and by providing a feature (power supply 42 in FIG. 2) enabling adjustment of the static magnetic field amplitude.

The chamber 30 includes a double shield 64 on its exterior surface. An active magnetic shield 62, which may be in the form of open wire loops coupled to a power supply or to the power supply (42 in FIG. 2) used to energize the magnet so as to have a magnetic field opposite in polarity to the static magnetic field induced inside the chamber 30 reduces the amplitude of the static magnetic field external to the chamber 30. An RF shield 60, which may be in the form of copper wire mesh, is disposed externally to the magnet poles 46 and service to reduce the amount of RF energy radiating outside the chamber 30.

Figure 4:
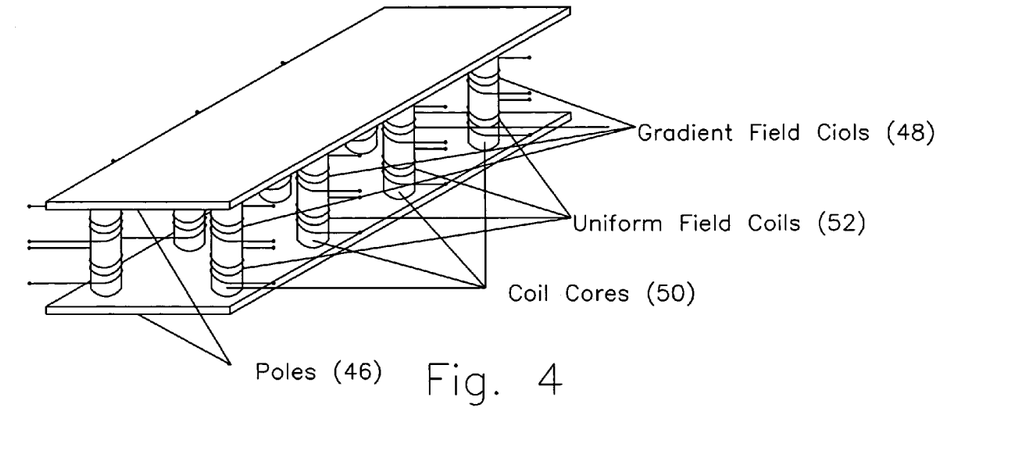
FIG. 4 shows one embodiment of a magnet used with the device shown in FIG. 2.

The magnet is shown in oblique view in FIG. 4. The poles 46 may be formed from sheets of ferromagnetic material such as steel. The coil supports 50 are disposed along the length of the poles 46 on the lateral edges thereof. The coil supports 50 may include both the homogeneous field coils 52 and gradient field coils 48.

In some embodiments, the magnet may include one or more permanent magnets (not shown) polarized in the same direction as the longitudinal axis of the coil supports 50 to supplement or replace of the static magnetic field induced by the homogeneous field coils 52. In such embodiments, the homogeneous field coils 52 would be used only to vary the amplitude of the homogeneous static magnetic field. Even in the present embodiment, which uses low static magnetic field amplitude, the field distribution and/or amplitude may be altered by the presence of certain materials and objects inside the chamber (30 in FIG. 2), and NMR signals may shift in frequency or disappear altogether. In such cases, in the present embodiment it is possible to quickly change the static magnetic amplitude field by changing the current flowing in the homogeneous field coils 52. In some embodiments, a total received NMR signal magnitude is determined, irrespective of any other analysis of the NMR signals, and the current flowing through the homogeneous field coils 52 may be adjusted to change the corresponding static magnetic field amplitude to maximize the total NMR signal amplitude. Such provision may enable correction of the NMR measurements for the presence of ferromagnetic and/or electrically conductive materials in the items being screened in the NMR screening device (20 in FIG. 1).

In a method according to one aspect of the invention, the computer, acquisition system and pulse programmer (see FIG. 2) may be configured to perform nuclear magnetic resonance relaxometry measurements on personal items disposed inside the chamber (30 in FIG. 2). Relaxometry measurements may be made using well know RF pulse sequences, such as Carr-Purcell-Meiboom-Gill (CPMG). The relaxometry measurements may be made in several distinct types to assess possible presence in a closed container of a safety threat (hazardous liquid). How the various types of measurements are made and the reasons therefore will be better understood with reference to FIGS. 5, 6 and 7.

Figure 5:
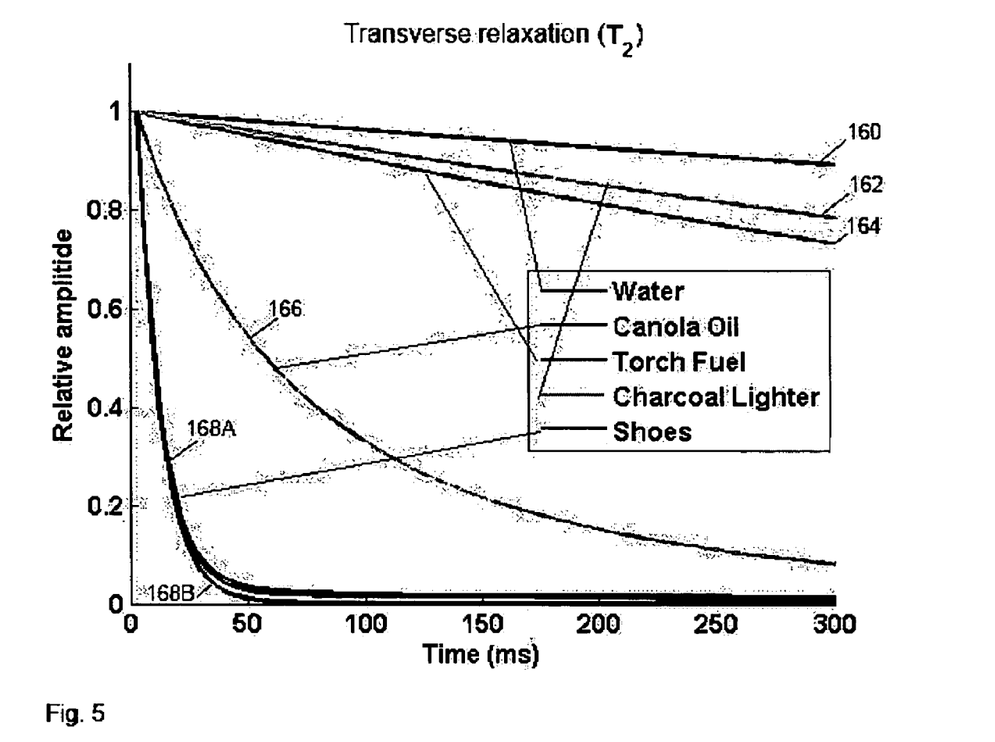
FIG. 5 shows graphs of transverse nuclear magnetic relaxation of various liquids and one solid material.

FIG. 5 shows transverse ($T_2$) relaxation curves for various liquids, including water 160, canola oil 166, commercially available "torch fuel" (or lantern fuel) 164, charcoal lighter fluid 162, and as solids, shoes, at curves 168A and 168B. What is apparent from the curves shown in FIG. 5 is that solids have much shorter transverse relaxation than most liquids. Such difference in transverse relaxation time may be used in relatively short duration NMR measurement sequences (lasting approximately five seconds) to establish the presence of quantities of liquids in personal items exceeding a selected threshold amount (mass).

In a method according to the invention, personal items may be subjected to such short duration NMR measurement sequence to determine the presence of liquids exceeding a selected safe threshold mass. Such mass determination may be made by the spin echo amplitude decay rate in a CPMG or similar sequence. If no such amount of liquid is detected, the screened personal item may be discharged from the screening system. In the event the safe threshold mass of liquid is determined to be present, in some embodiments, the personal item may be subjected to additional NMR screening, as will be explained below with reference to FIGS. 6 and 7.

Figure 6:
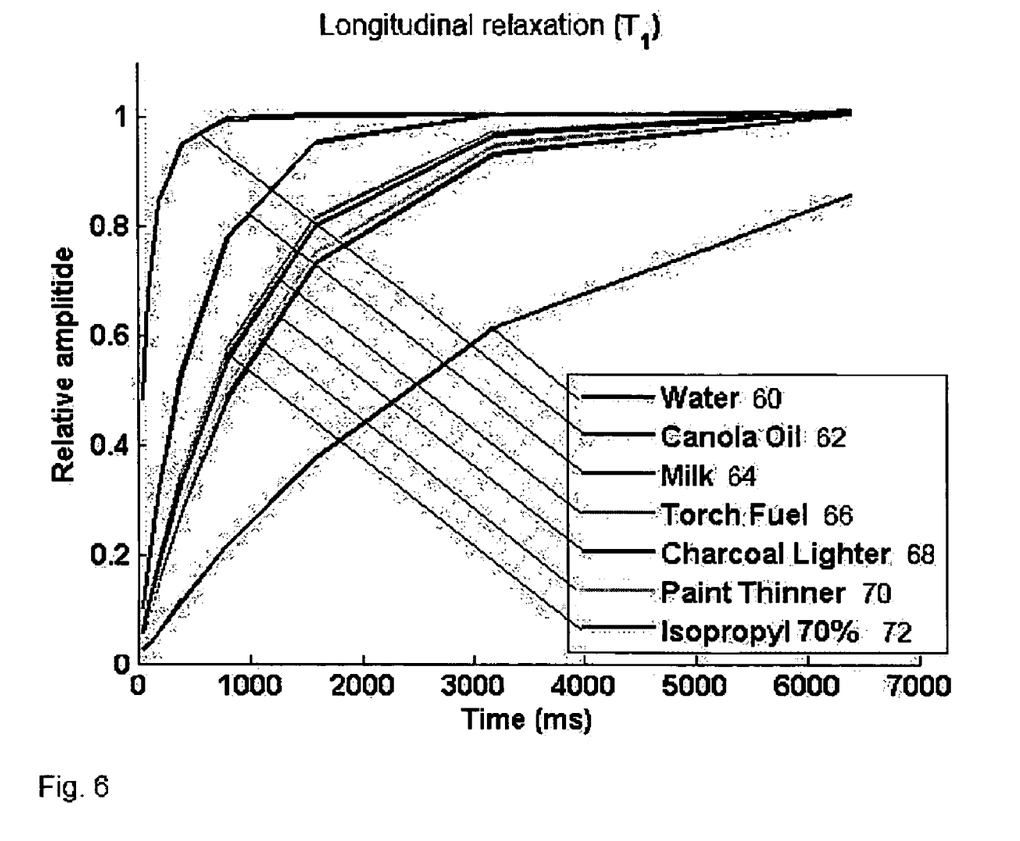
FIG. 6 shows graphs of longitudinal nuclear magnetic relaxation for various liquids.
Figure 7:
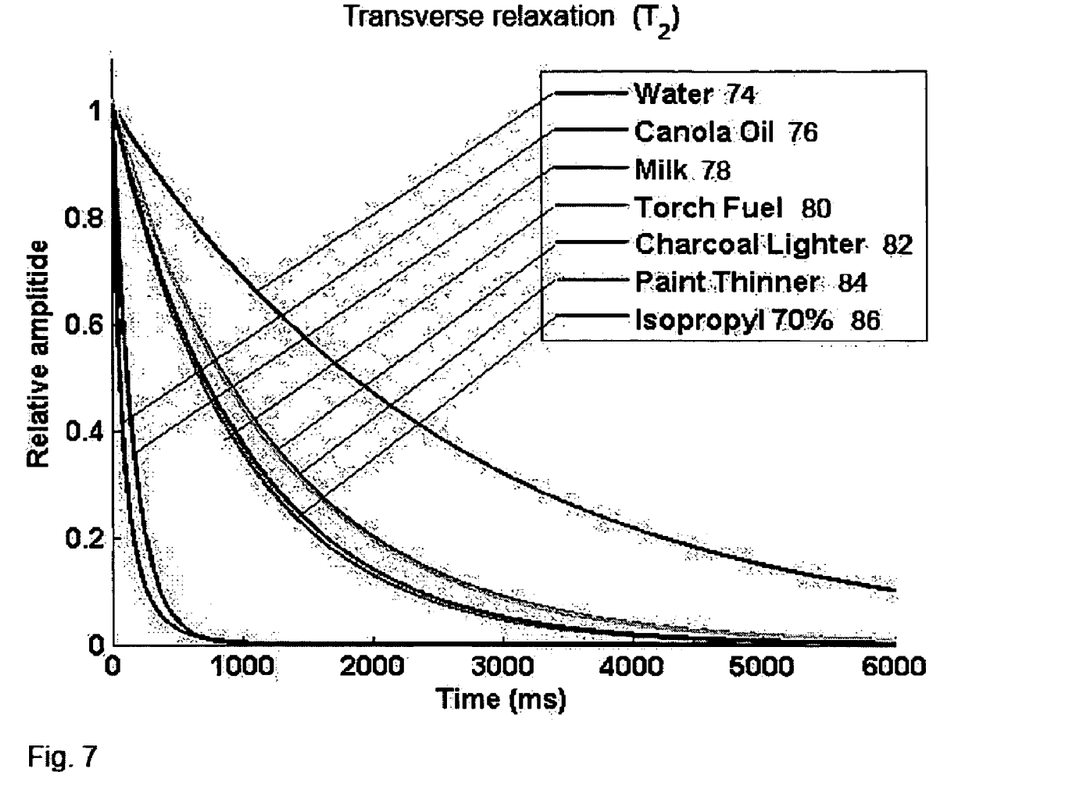
FIG. 7 shows graphs of transverse nuclear magnetic relaxation for various liquids.

FIG. 6 shows longitudinal ($T_1$) relaxation curves for various liquids, both hazardous and benign. The relaxation curves shown include those for water 60, canola oil 62, cow's milk 64, commercially available "torch fuel" or lantern fuel 66, charcoal lighter fluid 68, paint thinner (mineral spirits) 70 and 70% isopropyl alcohol 72. Of the example liquids, water has the slowest relaxation rate. FIG. 7 shows transverse ($T_2$) relaxation curves for similar substances including water 74, canola oil 76, milk 78, torch fuel 80, charcoal lighter fluid 82, paint thinner 84, and 70% isopropyl alcohol 86.

In the event a particular personal item is determined to have a liquid mass exceeding the selected threshold, the particular item may be subjected to a longer (approximately 30 seconds to two minutes) duration measurement sequence intended to perform the following analyses. First is to characterize the liquid present. As may be inferred from the foregoing graphs in FIGS. 6 and 7, determining the longitudinal and transverse relaxation rates for the liquids in the item can be used to estimate mass of various types of liquids in the item.

The apparatus shown schematically in FIG. 2 has the capacity to both to superimpose a selected gradient field to the homogeneous static magnetic field and to vary the RF operating frequency. Such capacity can provide the apparatus with at least a one dimensional capacity to estimate spatial distribution of the liquids detected in any personal item. By applying, for example, a linear gradient field along the direction of motion of the second conveyor (18 in FIG. 1) and performing CPMG sequences at a plurality of RF frequencies, it is possible to obtain relaxation measurements corresponding to various position along the chamber (30 in FIG. 2) where the total static magnetic field amplitude (homogeneous plus gradient) excites NMR phenomena at the particular RF frequency used in any one measurement sequence. Relative peak and/or average NMR signal amplitude at each position ("slice") may be mapped to estimate the spatial distribution of the detected liquid within the article. Another feature of the apparatus shown in FIG. 2 is that the gradient magnetic field provides the capacity to estimate diffusion properties of any detected liquids.

The combination of measurements made in the more complete scan ($T_1$, $T_2$, diffusion and spatial distribution) may be combined to assess a total threat level. The total threat level may be related to the type of liquid detected, its total mass and its spatial distribution. For example, certain mass of flammable liquids (lighter fuel, for example) distributed in particular patterns consistent with a container usually associated with such liquid (a cigarette lighter) may indicate a threat sufficiently high to warrant opening and visual inspection of the personal item fond to have contained such materials.

Figure 8:
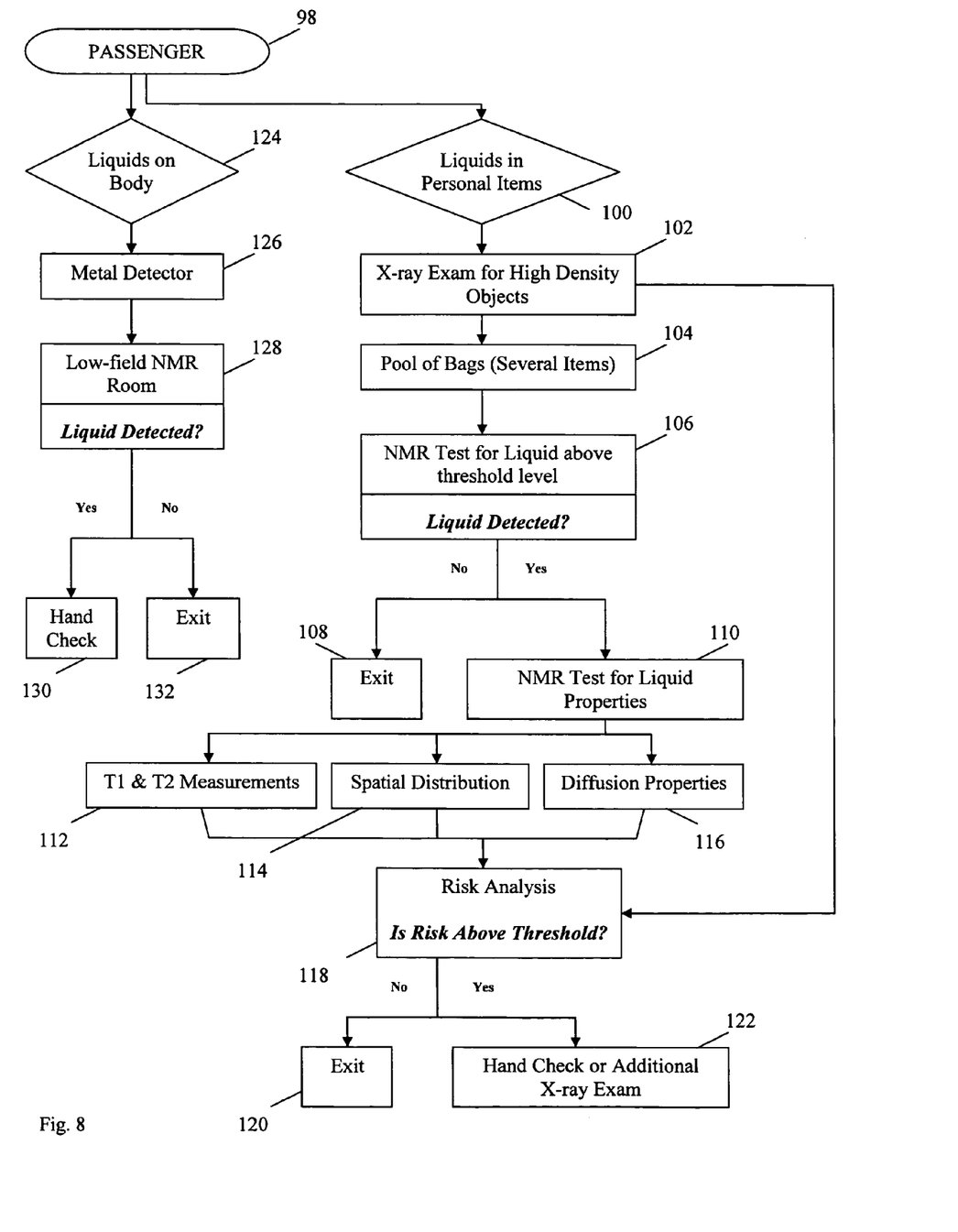
FIG. 8 is a flow chart of logical decisions for establishing existence of a threat in closed personal items and on persons according to one embodiment of an apparatus and methods according to the invention.

A process to identify threats using an apparatus such as shown in FIGS. 1 and 2 will now be explained with reference to a flow chart shown in FIG. 8. A passenger having at least one carry-on personal item enters the screening system at 98. A method and apparatus for searching the passenger's person will be further explained with reference to FIG. 9. The present description will focus on screening the at least one personal item, at 100. The item is first subjected to x-ray screening at 102 using the x-ray screening device (14 in FIG. 1). If the x-ray screen detects any suspicious object in the item, the item is dispatched, at 122, for visual inspection and is removed from the system (10 in FIG. 1). Items that are determined by x-ray not to have a suspicious item therein are moved at 102 to the pool 104 to await NMR screening. At 106, a short duration NMR scan is performed as explained above to determine presence of a threshold mass of liquid in the scanned item. If the liquid detection threshold is not exceeded, at 108, the scanned item is released and exits the system (10 in FIG. 1). If the liquid detection threshold is exceeded in a particular item, the particular item is then subjected to a rescan using the longer techniques explained above including $T_1$ and $T_2$ liquid composition analysis at 112, spatial distribution at 114 and diffusion properties at 116. The results of the additional scan are evaluated at 118 to determine if a liquid based threat is likely to exist in the particular item. If the risk is determined at 120 not to exceed a selected risk threshold, the item is discharged from the system and is returned to its owner or bailee. If the risk is determined to exceed a selected threshold, then the item may be dispatched for opening and visual inspection. In the event any one or more personal items are selected for more thorough NMR screening, personal items may be buffered in the pool (16 in FIG. 1) after leaving the x-ray scanner until which time as the NMR scanner is again available for more rapid liquid content scanning.

Using a method and system as described above, the number of personal items required to be opened for visual inspection can be substantially reduced. Personal items which do not contain hazardous materials in sufficient quantity to represent a danger to the aircraft are quickly and efficiently discharged from the screening system.

Figure 9:
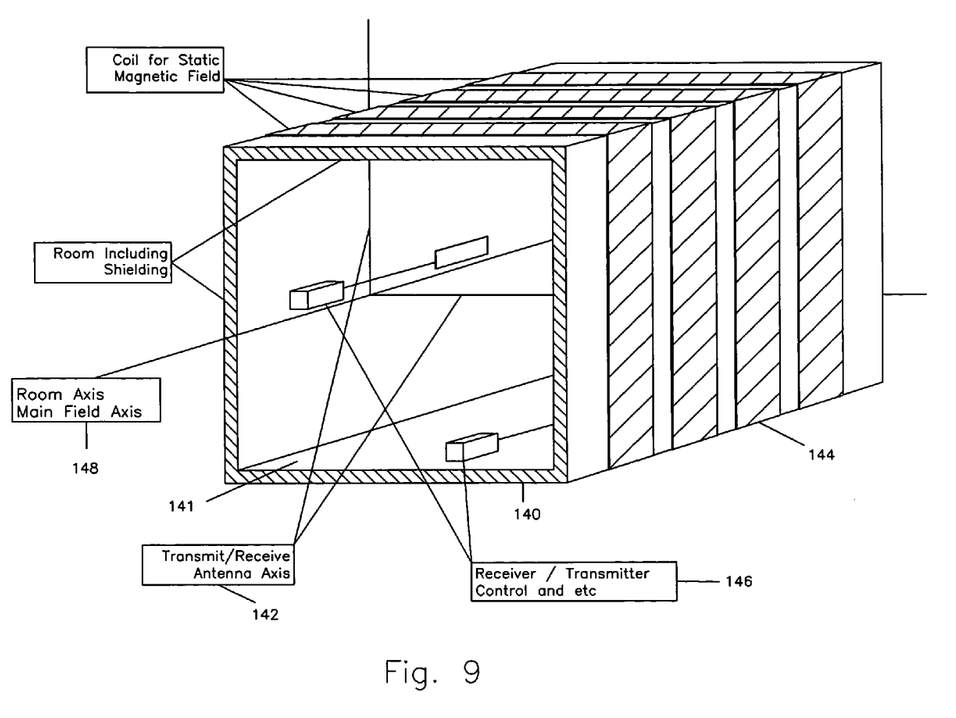
FIG. 9 is one embodiment of a system for whole body scanning according another aspect of the invention.

Passengers may be quickly and efficiently screened for the presence of liquids on their person by using a system as will be explained with reference to FIG. 9. The embodiment of a system according to FIG. 9 includes an electromagnet 144 which may be in the form of a wire coil wound so that its longitudinal axis is substantially coaxial with a longitudinal axis of an examination room 141. The room 141 is preferably made from non-magnetic, electrically non-conductive materials to avoid affecting the magnetic field induced by the magnet 144. The magnet 144 may be energized by the same or similar circuitry as shown in FIG. 2 and it induces a substantially homogeneous static magnetic field inside the room 141. Security system operators may use hand-held scanners, shown generally at 146, each of which includes a loop type antenna connected to transmit/receive circuitry. The transmit/receive circuitry may be operated wirelessly and under common control of an acquisition system substantially as shown in and explained with reference to FIG. 2. During examination of persons passing through the room 141, the hand held scanners 146 are moved proximate the persons being examined. The acquisition system (FIG. 2) operates each hand-held scanner 146 to substantially synchronously emit RF pulses and to detect NMR signals induced therein. NMR signals that when analyzed indicate presence of liquid on the person being examined may cause the system operator to order that the person is subjected to a more thorough examination, such as one conducted personally by a security officer.

Figure 9A:
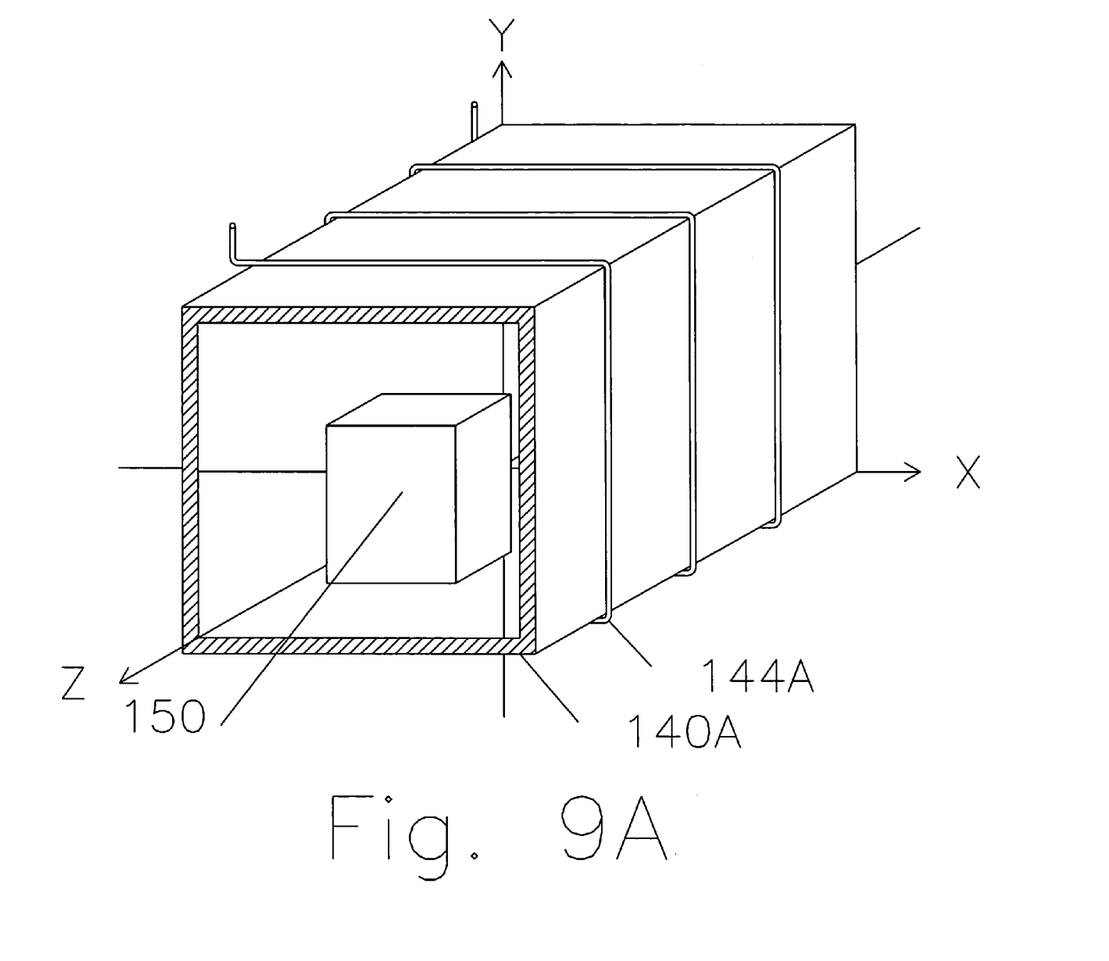
FIG. 9A shows one embodiment of a magnet arranged to induce a homogeneous static magnetic field in a room.

An alternative arrangement of a passenger scanning device for detecting liquids on the person of a human subject will now be explained with reference to FIGS. 9A, 9B and 10. FIG. 9A shows one embodiment of an electromagnet coil 144A that is wound around the exterior of a substantially non-magnetic room 140A. It should be noted that the size and configuration of the room 140A may be selected to enable inclusion in the room 140A of additional screening devices, such as air samplers used to infer presence of explosives and other materials that may be detected from air samples. It will be appreciated by those skilled in the art that such other screening devices are preferably non-magnetic. These devices should be non-electrically conductive if positioned within the RF magnetic field generated by transmitting antenna to avoid altering the characteristics of the RF magnetic fields. The electromagnet coil 144A is arranged such that at least one selected volume 150 within the room 140A will have induced therein a substantially homogeneous static magnetic field when electric current is passed through the coil 144A. In the present embodiment, the coil 144A may be arranged such that the static magnetic field is polarized along the axis indicated by z in FIG. 9A (the longitudinal axis of the room). The particular polarization direction of the magnetic field is not a limit on the scope of this invention, however, it will be appreciated that the selected polarization direction of the static magnetic field, and a radio frequency magnetic field to be induced as explained below enables building magnetic coils to provide free ingress and egress of persons to and from the room 140A and the volume 150 therein. Electric current to energize the electromagnet coil 144A may be supplied by an NMR measurement system configured such as shown and explained with reference to FIG. 2, for example. In the present embodiment, the amount of current passed through the coil 144A is selected such that the static magnetic field amplitude generally does not exceed about 5 Gauss anywhere in the room 140A. Such field amplitude will enable the room 140A to be used safely for NMR measurement substantially without shielding, and will enable passage through the room of persons using electronic medical devices such as pacemakers. Currently, in airport screening environments the use of metal detectors is considered essential. Use of these metal detectors is prohibited for people wearing certain medical devices such as pacemakers. Work is underway to make all pacemakers compatible with magnetic resonance imaging devices and metal detectors. In the event such pacemakers are developed, the amount of current passed through the coil 144A may be selected such that the static magnetic field amplitude may exceed 5 Gauss in the room 140A. Practical values for static magnetic field amplitude are in the range of 5 to 50 Gauss.

Figure 9B:
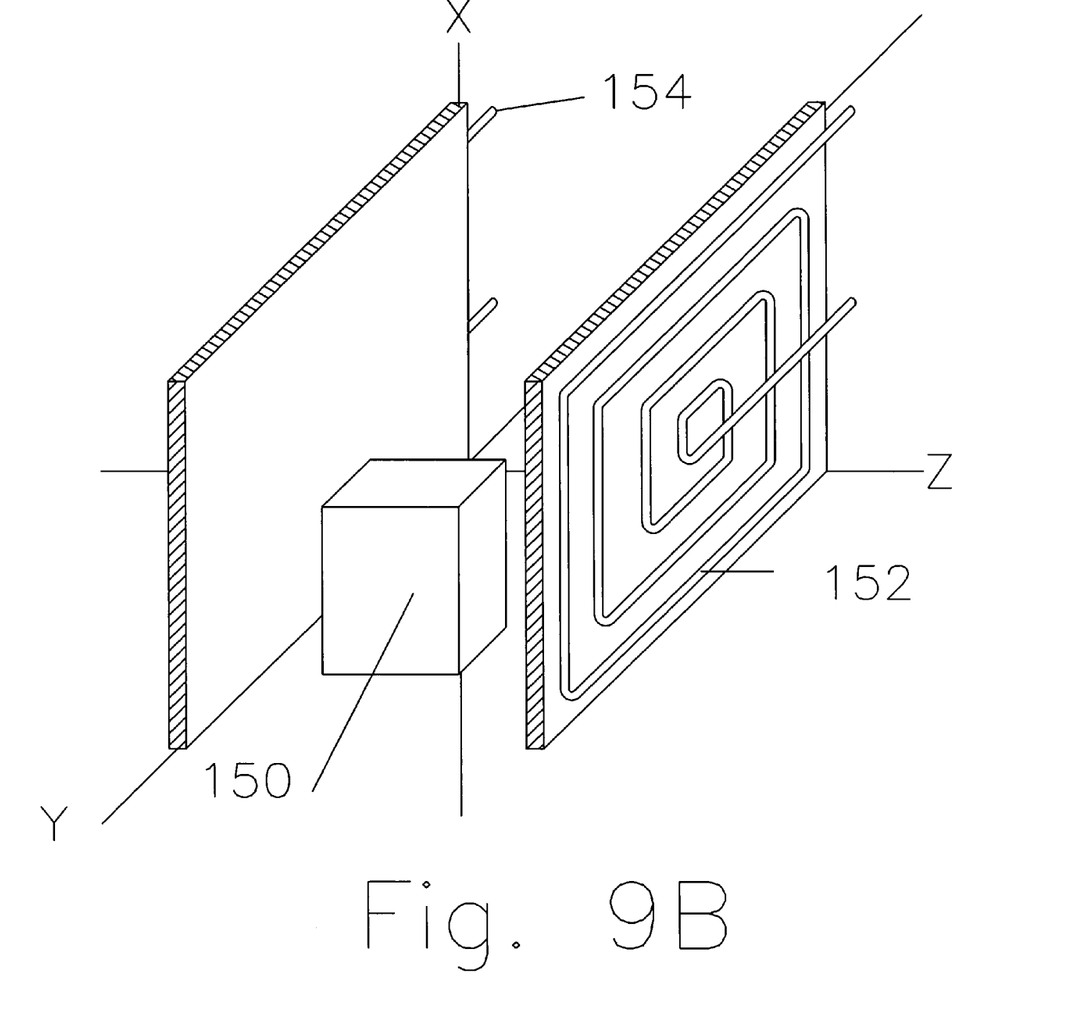
FIG. 9B shows one embodiment of RF antennas arranged to induce a homogenous RF magnetic field in a room.

FIG. 9B shows an RF magnetic field antenna coil 152 disposed proximate one wall of the room (140A in FIG. 9A). A corresponding RF magnetic field coil 154 is disposed proximate the other wall of the room (140A in FIG. 9A). The RF antenna coils 152, 154 may be arranged such that when suitably energized a radio frequency magnetic field is induced in the selected volume 150 that is substantially perpendicularly polarized with respect to the static magnetic field. Suitable energizing of the RF antenna coils 152, 154 may be obtained using a system such as shown and explained with reference to FIG. 2, for example. The frequency used to energize the RF antenna coils 152, 154 is selected to induce NMR phenomena in selected nuclei of persons passed through the volume 150. As in the other embodiments described herein, such nuclei are typically hydrogen. The NMR system may use pulsed radio frequency power to induce any form of detectable nuclear magnetic resonance phenomena suitable for determining mass of liquid present on a human subject disposed within the volume 150.

In the present embodiment, the RF antenna coils 152, 154 may be used only to induce the RF magnetic field within the volume 150. Referring now to FIG. 10, an arrangement of RF electromagnetic field detector antennas will be explained. A first loop antenna 155 may be disposed in a fixed position within the volume (150 in FIG. 9A) and arranged such that its magnetic dipole is perpendicular to the polarization direction of the static magnetic field, and may be parallel to the polarization of the RF magnetic field induced by the RF antenna coils (152, 154 in FIG. 9B). The first loop antenna 155 encloses an area that is at least as large as the frontal area of the largest expected human subject to enter the room (140A in FIG. 9A) for scanning. Within the area defined by the first loop antenna 155, or alternatively to the first loop antenna 155, a plurality of smaller loop antennas 156 may be arranged along a substantially planar surface such that their magnetic dipole moments are parallel to those of the RF magnetic field antenna coils (152, 154 in FIG. 9B) and perpendicular to the static magnetic field. Collectively, the loop antennas 156 may cover substantially the same area as defined by the first loop antenna 155 and may be substantially contiguous. For purposes of the invention, a suitable size for each of the smaller loop antennas 156 may be about 2 inches square. In a typical implementation, there would be an array of approximately twenty by forty such smaller loop antennas 156 substantially contiguously arranged along the substantially planar surface. Each such loop antenna 156 may have connected to its terminals its own RF receiver circuitry, that may be substantially as explained with reference to FIG. 2. The loop antennas 155 and/or 156 are used to detect NMR signals originating proximate the body surface of a human subject 161 being scanned for the presence of liquids on his person.

A substantially similar arrangement of loop antennas including a second loop antenna 155A, and/or smaller loop antennas 156, may be arranged on a movable surface 157. The antennas 155A, 156 on the movable surface 157 may be arranged such that their magnetic dipole moments are parallel to the dipole moments of the RF antenna coils (152, 154 in FIG. 9B). The movable surface 157 may be made from a substantially non magnetic, electrically non-conductive material. A conveyor 158 may move the movable surface 157 into proximity with a human subject 161 disposed between the two loop antennas 155, 155A (or arrays 156 alone if the large loop antennas are omitted). A proximity detector 160 such as a laser, capacitance or acoustic proximity detector may provide a signal that the movable surface 157 is proximate the human subject 161. The conveyor and proximity detector 160 may be in signal communication with a controller in a system such as explained with reference to FIG. 2. In such embodiments, the system controller (FIG. 2) may operate the conveyor 158 as each human subject 161 enters the area disposed between the antennas 155, 155A to move the movable surface 157 until it is proximate the human subject 161. It is contemplated that the human subject 161 will stand with his back (or front) facing the first loop antenna 155 and the movable surface 157 will come into proximity with the opposed face of the human subject 161. The RF antenna coils (152, 154 in FIG. 2) are then energized to induce NMR phenomena in the human subject 161. Due to the low static magnetic field amplitude and corresponding low RF frequency used, it is expected that detectable NMR signals will originate generally proximate the body surfaces of the human subject 161. NMR signals originating proximate each body surface of the human subject 161 will be detected in the various loop antennas 155, 155A, 156. The detected signals may be conducted to appropriate receiver channels in an NMR system as shown and explained with reference to FIG. 2. Signal amplitudes indicative of the presence of liquids present on the person of the human subject 161 may be analyzed so as to determine the total quantity and/or the spatial distribution of such liquids about the person of the human subject 161. Total quantity and/or distribution of liquids indicative of a security threat may cause the system operator to direct the human subject to appropriate additional security screening procedures. It is also within the scope of this invention to analyze the NMR signals to determine whether the detected liquid is hazardous or non hazardous, substantially as explained with reference to FIGS. 5 through 7.

Figure 10:
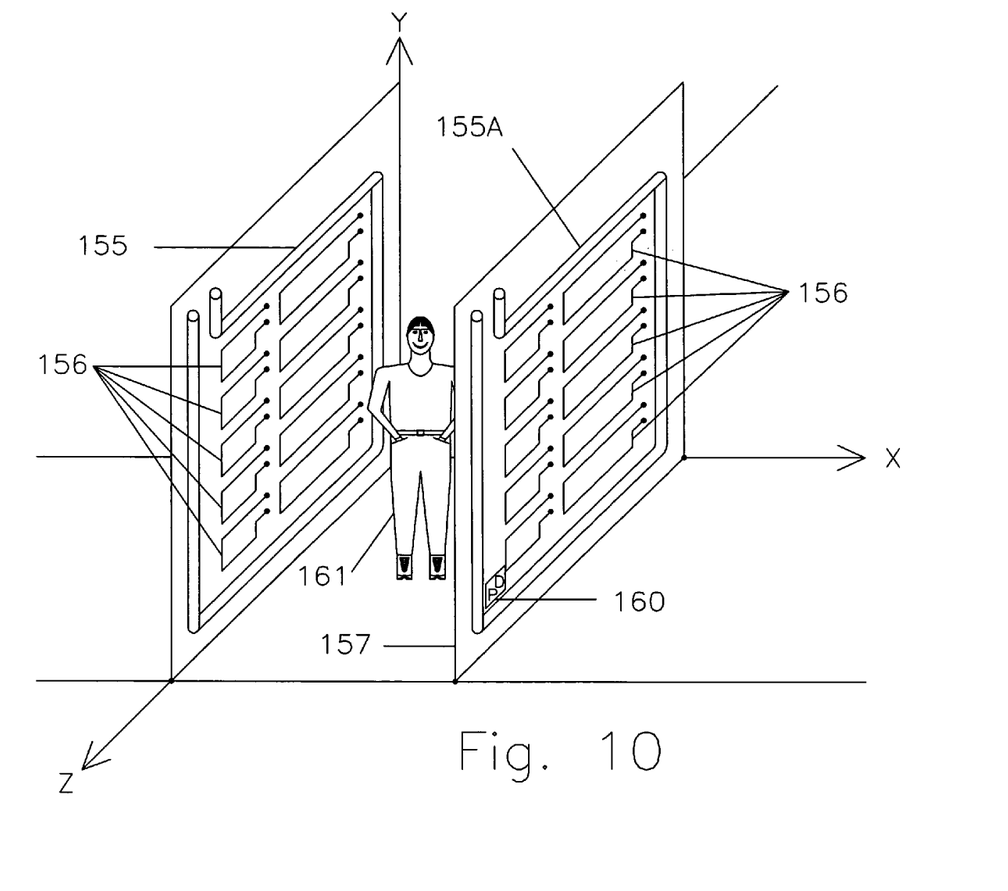
FIG. 10 shows one embodiment of arrays of RF receiver antennas arranged to determine presence of threshold mass of liquids on a human subject, and arranged to determine distribution of liquids on the human subject.

Using a movable surface as shown in FIG. 10 may provide the system with the capability to detect distributed liquids on a wide range of different size human subjects conveniently and more quickly than using a single RF receiver antenna coil or array of such coils as shown, respectively, at 155 and 156 in FIG. 10.

Referring once again to FIG. 8, at 98, a human subject enters the room (140A in FIG. 9) and stands face forward or back against the fixed one of the receiver antennas (155, 156 in FIG. 9B) for detection of liquids, at 124, on his person. In embodiments including the movable surface (157 in FIG. 9B), such movable surface having the other receiver antenna thereon is moved proximate the human subject. NMR scanning is performed as explained above. Metal detection 126 may be performed before or after NMR scanning. At 128, if a threshold mass of liquid is detected by the NMR scanning, the human subject, at 130 may be subject to further security screening. If no threshold mass of liquid is detected by the NMR screening, then at 132 the human subject is released from further personal security screening, or, if performed in such order, is subject to metal detection at 126.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for screening personal items for presence of safety hazards, comprising:
   x-ray scanning the personal articles for presence of high-density objects;
   nuclear magnetic resonance scanning the personal articles for presence of liquids above a threshold mass;
   nuclear magnetic resonance scanning the personal articles to estimate composition of liquids detected above the threshold mass;
   nuclear magnetic resonance scanning the personal articles to determined spatial distribution of liquids detected above the threshold mass; and
   selecting ones of the personal items for opening and inspection if the x-ray scanning and, nuclear magnetic resonance scanning for liquids above the threshold mass, nuclear magnetic resonance scanning for composition and nuclear magnetic resonance scanning for spatial distribution indicates a combined threat level above a selected threshold.

2. The method of claim 1 further comprising nuclear magnetic resonance scanning the personal items to estimate composition of liquids detected above the threshold mass; and
   selecting ones of the personal items for opening and inspection if the x-ray scanning, nuclear magnetic resonance scanning for liquids above the threshold mass and nuclear magnetic resonance scanning for composition indicates a combined threat level above a selected threshold.

3. The method of claim 1 further comprising nuclear magnetic resonance scanning the personal items to determined spatial distribution of liquids detected above the threshold mass; and
   selecting ones of the personal items for opening and inspection if the x-ray scanning, nuclear magnetic resonance scanning for liquids above the threshold mass and nuclear magnetic resonance scanning for spatial distribution indicates a combined threat level above a selected threshold.

4. A system for screening human subjects for presence of liquids, comprising:

a room sufficiently large to enable free ingress and egress of a largest expected human subject;

at least one electromagnet coil wound to induce a substantially homogeneous static magnetic field along a selected direction within a selected volume within the room;

at least one radio frequency antenna configured to induce a substantially homogeneous radio frequency magnetic field in the selected volume along a direction substantially perpendicular to the selected direction of the static magnetic field;

means for energizing the at least one electromagnet coil and the at least one radio frequency antenna to induce respective the static and the radio frequency magnetic fields;

a first receiver antenna configured to detect nuclear magnetic signals originating proximate a first face of a human subject disposed proximate thereto;

means for analyzing the detected signals to determine presence of at least a threshold mass of liquid proximate the first face of the human subject.

5. The system of claim 4 wherein the first receiver antenna comprises a plurality of antenna loops arranged on a substantially planar surface, and wherein the means for analyzing comprises means for analyzing nuclear magnetic resonance signals detected by each of the antenna loops such that a distribution of liquid about the first face of the human subject is determinable.

6. The system of claim 4 wherein the means for energizing is configured such that a maximum static magnetic field amplitude is about five Gauss.

7. The system of claim 4 wherein the means for energizing is configured such that a static magnetic field amplitude is in the range of 5 to 50 Gauss.

8. The system of claim 4 wherein further comprising a second receiver antenna is disposed on a movable surface, the movable surface under functional control of a proximity detector, the detector and movable surface configured such that the movable surface stops when proximate the human subject, the second receiver antenna functionally coupled to the means for analyzing signals such that at least one of a mass and a distribution of liquid on a second face of the human subject opposed to the first face is determinable.

9. A method for screening a human subject for presence of liquids, comprising:

inducing nuclear magnetic resonance phenomena in selected nuclei associated with liquids proximate to the surface of the body of the human subject;

detecting nuclear magnetic resonance signals originating proximate the surface of the human subject; and analyzing the detected signals to determine at least one of presence of a threshold mass of liquid and a spatial distribution of liquid about the person of the human subject.

10. The method of claim 9 wherein the inducing nuclear magnetic resonance phenomena comprises inducing a substantially homogeneous static magnetic field in the human subject, the static magnetic field having an amplitude of at most about five Gauss.

11. The method of claim 9 wherein the detecting nuclear magnetic resonance signals comprises detecting radio frequency electromagnetic energy within each of a plurality of individual receivers antennas distributed about a surface area of the human subject.

12. The method of claim 11 wherein the determining spatial distribution comprises analyzing signals detected by each of the plurality of receiver antennas.

13. The method of claim 9 further comprising performing metal detection on the human subject.

* * * * *